(12) United States Patent
Leiner et al.

(10) Patent No.: US 8,968,000 B2
(45) Date of Patent: Mar. 3, 2015

(54) MIXING AND APPLICATION CAPSULE FOR PRODUCING A DENTAL PREPARATION

(75) Inventors: Uwe Leiner, Midlum (DE); Manfred Thomas Plauman, Cuxhaven (DE)

(73) Assignee: VOCO, GmbH, Cuxhaven (DE)

( * ) Notice: Subject to any disclaimer, the term of this patent is extended or adjusted under 35 U.S.C. 154(b) by 717 days.

(21) Appl. No.: 12/755,029

(22) Filed: Apr. 6, 2010

(65) Prior Publication Data

US 2010/0261139 A1 Oct. 14, 2010

(30) Foreign Application Priority Data

Apr. 8, 2009 (DE) .......................... 10 2009 016 862

(51) Int. Cl.
*A61C 5/04* (2006.01)
*A61M 37/00* (2006.01)
*A61C 5/06* (2006.01)

(52) U.S. Cl.
CPC ................. *A61C 5/062* (2013.01); *A61C 5/064* (2013.01)
USPC ....................................... 433/90; 64/87; 64/88

(58) Field of Classification Search
CPC ........ A61C 5/062; A61C 5/066; A61C 5/064; A61C 5/068; A61C 9/0026; A61C 15/043; A61C 19/063
USPC ........... 206/63.5, 219, 221; 222/83, 136, 570, 222/145.1, 145.5, 342, 378, 386, 386.5, 222/406, 407, 424.5, 527, 533, 534; 366/139, 176; 433/89, 90; 604/218, 604/311, 191, 82, 86–89, 200–201, 203, 604/205, 207, 244, 251–253
See application file for complete search history.

(56) References Cited

U.S. PATENT DOCUMENTS

| 4,648,532 | A | * | 3/1987 | Green ............................. 222/82 |
| 4,674,661 | A | * | 6/1987 | Herold .......................... 222/386 |
| 4,863,017 | A | | 9/1989 | Vlock |
| 4,941,751 | A | * | 7/1990 | Muhlbauer ................ 366/182.1 |
| RE33,801 | E | * | 1/1992 | Green ............................. 222/82 |

(Continued)

FOREIGN PATENT DOCUMENTS

| DE | 3920537 A1 | 2/1990 |
| DE | 93 03 268 U1 | 7/1994 |

(Continued)

*Primary Examiner* — Cris L Rodriguez
*Assistant Examiner* — Matthew Nelson
(74) *Attorney, Agent, or Firm* — Duane Morris LLP; J. Rodman Steele, Jr.; Gregory M. Lefkowitz

(57) ABSTRACT

A mixing and application capsule for producing and discharging a dental preparation is disclosed. In order to prevent a liquid loss, a mixing and application capsule for producing a dental preparation is proposed according to the invention, which has: a capsule body (31) with a mixing chamber (32) for receiving a mixing component (41) and for mixing the dental preparation (43) from the mixing component (41) and a fluid (42) and with an outlet opening (33) for discharging the dental preparation (43), a first plunger body (11) which can be displaced in the capsule body (31), delimits the mixing chamber (32) in the capsule body (31) and has a channel (19) to guide the fluid (42) from a cavity (22) into the mixing chamber (32) and a projection (12), and a second plunger body (21) which can be displaced in the capsule body (31) relative to the first plunger body (11) and has the cavity (22) to receive the fluid (42), the cavity (22) being configured to receive the projection (12) of the first plunger body (11).

15 Claims, 18 Drawing Sheets

(56) References Cited

U.S. PATENT DOCUMENTS

| | | | | |
|---|---|---|---|---|
| 5,172,807 A | * | 12/1992 | Dragan et al. | 206/219 |
| 5,392,904 A | * | 2/1995 | Frick et al. | 206/219 |
| 5,599,312 A | * | 2/1997 | Higashikawa | 604/191 |
| 5,871,355 A | | 2/1999 | Dragan | |
| 6,152,296 A | * | 11/2000 | Shih | 206/222 |
| 6,386,872 B1 | * | 5/2002 | Mukasa et al. | 433/90 |
| 6,846,300 B2 | * | 1/2005 | Horth et al. | 604/85 |
| 7,311,195 B2 | * | 12/2007 | Schmid | 206/219 |
| 7,481,333 B2 | * | 1/2009 | Goldberg et al. | 222/135 |
| 7,748,567 B2 | * | 7/2010 | Horner et al. | 222/135 |
| 2001/0053511 A1 | * | 12/2001 | Aoyagi et al. | 433/90 |
| 2002/0098462 A1 | * | 7/2002 | Kaneko et al. | 433/89 |
| 2002/0160333 A1 | * | 10/2002 | Pierson et al. | 433/90 |
| 2004/0104133 A1 | * | 6/2004 | Aoyagi et al. | 206/63.5 |
| 2006/0113201 A1 | * | 6/2006 | Micic et al. | 206/221 |
| 2007/0211563 A1 | * | 9/2007 | De Vries | 366/139 |
| 2007/0272567 A1 | * | 11/2007 | Peuker et al. | 206/219 |
| 2009/0236303 A1 | * | 9/2009 | Lizerbram et al. | 215/227 |

FOREIGN PATENT DOCUMENTS

| | | |
|---|---|---|
| DE | 19906887 C1 | 7/2000 |
| EP | 1 759 657 A2 | 3/2007 |
| WO | 03/028871 | 4/2003 |

* cited by examiner

MIXING AND APPLICATION CAPSULE FOR PRODUCING A DENTAL PREPARATION

CROSS-REFERENCE TO RELATED APPLICATIONS

This application claims priority to German Application no. 10 2009 016 862.1, filed Apr. 8, 2009, which is incorporated herein by reference in its entirety.

BACKGROUND

The present invention relates to a mixing and application capsule for producing a dental preparation.

Mixing and application capsules allow a mixing of solid and fluid components in order, for example, to produce a dental preparation, which is then applied from the mixing and application capsule in the oral cavity of the patient. In order to produce glass ionomer cement, for example, a powder component is mixed with a liquid component. Various methods are known in the prior art to accommodate the liquid which is mixed on activation of the mixing and application capsule with the powdery component in order to produce the dental preparation.

The liquid is accommodated, for example, in a foil pouch, which is opened by bursting. The foil pouch is then squeezed out in order to press the liquid out of it and feed it to the powdery component. This method has the disadvantage that with a pouch which is very long in relation to the pouch diameter, in particular, the foil produces folds when being squeezed together, in which an indeterminate liquid residue remains. The result is that the dental preparation compound is mixed with too little fluid, so it does not have the desired properties. Therefore, either the size of the foil pouch and thus the liquid quantity are limited or else the dosage is imprecise. The diameter of the foil pouch cannot generally be varied as desired as the capsule would have to have a correspondingly larger diameter. A capsule with a larger diameter is, however, disadvantageous on application in the oral cavity of a patient. Also, the squeezing-out tongs used when squeezing out the mixing and application capsule are generally adapted for small capsule diameters.

A variation is that a foil pouch is arranged laterally on or at the capsule body. A pouch of this type may therefore have a significantly larger diameter and liquid quantity. However, the disadvantage exists that a separate activation tool is necessary to open the foil pouch and to bring its content in the capsule in contact with the powder (i.e. to activate the capsule). Also, proportionally more liquid remains in a pouch with a large diameter.

A further example of accommodating a liquid in a mixing and application capsule for producing a dental preparation is described in U.S. Pat. No. 6,386,872 B1. Arranged in the interior of the capsule body are a first and a second plunger, in the intermediate space of which a liquid is arranged. The first plunger delimits the mixing chamber in the interior of the plunger body, in which the powdery component is arranged. The plunger wall between the mixing chamber and liquid chamber has a desired breaking point. If the second plunger is pushed in the direction of the mixing chamber, a projection of the second plunger breaks through the desired breaking point of the wall of the first plunger, so the liquid flows into the mixing chamber in order to be mixed there with the powdery component. After the activation, for example in that the capsule is pressed by hand onto a table surface, the capsule has to be clamped into a mixing apparatus, which mixes the powder and liquid to form a paste by means of shaking movements. The capsule is then clamped in squeezing-out tongs, with the aid of which the two plungers are moved further forward. The paste is discharged in the process through the cannula and, for example, used to fill a cavity of a tooth to be treated.

The arrangement according to U.S. Pat. No. 6,386,872 B1 has the disadvantage that diffusion losses of the liquid exist and the mixing and application capsule is therefore not suitable to be stored over a relatively long time period. The seal between the first and the second plunger is a sliding seal. If the seal is selected to be smooth-running, so a displacement of the second plunger relative to the first plunger is possible manually, there is an insufficient seal and the liquid can evaporate between the first and second plunger. If the seal is selected to be so tight that evaporation of the liquid through the seal is virtually completely avoided, the second plunger can only be displaced relative to the first plunger with the application of a large force which requires special tools and is no longer possible manually. Furthermore, a similar problem of liquid evaporation exists for the seal between the first plunger and the capsule body. The powdery component in the mixing chamber is hygroscopic and therefore tends to absorb moisture entering through the seal between the first plunger and capsule body. This also impairs the long-term storability of the mixing and application capsule. In addition, the thin-walled desired breaking point region of the wall of the first plunger is easy for the liquid to penetrate. The powdery component can therefore not only absorb moisture from the liquid via the seal between the first plunger and capsule body, but also through the desired breaking point region of the wall of the first plunger.

Further examples, also with a sliding seal are to be found, for example, in EP 1 226 790 or also in JP 2001340356.

WO 03/028871 A1 discloses a mixing capsule for a two-component mixing with a cylindrical container part and a spray nozzle molded onto the end face. A plunger is axially displaceably guided in the container part. Provided in the end face of the plunger is an opening adjoined by a liquid receptacle with a burstable wall or membrane. When the capsule is not activated, the membrane seals the opening. The cavity between the end faces of the container part and the plunger forms a mixing chamber. A movable activating part is provided in the mixing chamber. The activating part can be displaced by means of an activating pin sealing the spray nozzle in the non-activated state. In the activated state of the capsule, the activating part is substantially completely received in the liquid receptacle.

SUMMARY OF THE INVENTION

The invention is based on the object of providing a mixing and application capsule which eliminates the above-mentioned disadvantages of the prior art.

According to the invention, the object is achieved by a mixing and application capsule for producing a dental preparation, the mixing and application capsule having:
- a capsule body with a mixing chamber for receiving a mixing component and for mixing the dental preparation from the mixing component and a fluid and with an outlet opening for discharging the dental preparation,
- a first plunger body which can be displaced in the capsule body, delimits the mixing chamber in the capsule body and has a channel to guide the fluid from a cavity into the mixing chamber and a projection, and
- a second plunger body which can be displaced in the capsule body relative to the first plunger body and has the cavity to receive the fluid, the cavity being configured to receive the projection of the first plunger body.

The invention is based on the idea that the first plunger body is a double plunger, the projection of the first plunger of the double plunger being configured to press out a content of the cavity and the delimitation to the mixing chamber being configured as a second plunger of the double plunger. The mixing and application capsule is preferably configured as a telescopic cylinder, the first plunger body being a first cylinder and the second plunger body being a second cylinder, the first cylinder being telescopically displaceable in the capsule body and the second cylinder being telescopically displaceable in the first cylinder. On activation of the mixing and application capsule, a relative movement is carried out between the first and second plunger body, the projection of the first plunger body acting as a ram and filling up the cavity of the second plunger body in such a way that its content is pressed out. Correspondingly, the projection of the first plunger body is preferably a ram, which is configured such that if the ram is introduced into the cavity a content located in the cavity is displaced and the cavity is emptied. It is further preferred for the positive shape of the projection of the first plunger body to correspond to the negative shape of the cavity receiving the liquid or for the negative shape of the cavity receiving the liquid to correspond to the positive shape of the projection of the first plunger body. When discharging the dental preparation, the end of the first plunger body delimiting the mixing chamber acts as a plunger to push out the mixed dental preparation from the capsule body. Accordingly, a preferred mixing and application capsule according to the invention has: a capsule body with a mixing chamber for receiving a mixing component and for mixing the dental preparation from the mixing component and a liquid and with an outlet opening for discharging the dental preparation, a liquid container with a cavity for receiving the liquid and a double plunger body, which is arranged between the mixing chamber and the liquid container, and a channel for guiding the liquid from the cavity into the mixing chamber, the double plunger body at the first end facing the liquid container being configured to push a liquid arranged in the cavity out of the cavity so the liquid is removed into the channel, and wherein the double plunger body at the second end facing the mixing chamber is configured to push a dental compound produced in the mixing chamber out of the outlet opening.

Owing to the configuration according to the invention of the mixing and application capsule, a particularly tight liquid barrier is achieved. The capsule according to the invention provides the advantage that the liquid, which is arranged in a cavity in the second plunger body, cannot evaporate through the seal between the first and second hollow body. A smooth-running manual displaceability of the second plunger body relative to the first plunger body is also ensured. The mixing and application capsule according to the invention also provides the advantage that the liquid is prevented from diffusing through the first plunger body and mixing with the component in the mixing chamber, as the side facing the powder is, for example, sealed with a barrier layer foil and is therefore not permeable.

A further advantage of the mixing and application capsule according to the invention is that the foil sealing the cavity tears open abruptly when opened depending on the embodiment, so the liquid is sprayed at a high speed into the powder component. Incomplete emptying of the liquid can thus be avoided.

A further advantage of the mixing and application capsule according to the invention is that the use of a deformable foil pouch can be dispensed with. As, on activation of the mixing and application capsule according to the invention, the projection of the first plunger body is received in the cavity of the second plunger body, the fluid is completely pressed out of the cavity. The mixing ratio can thus be adhered to very precisely. The liquid quantity is also less severely limited as the cavity in the second plunger body can be selected to be correspondingly deep.

A further advantage of the mixing and application capsule according to the invention is that no separate tool is required for activation as the activation takes place by applying a pressure to the second plunger body.

Furthermore, the handling of the mixing and application capsule is particularly simple as the two plunger bodies are displaced in one and the same direction within the mixing and application capsule according to the invention to activate the mixing and application capsule and then discharge the dental preparation. This advantage is achieved, in particular, in that the end of the first plunger body delimiting the mixing chamber, when the dental preparation is discharged, acts as a plunger to push the mixed dental preparation out of the capsule body.

The cavity is preferably configured to receive a liquid capsule. A liquid capsule is preferably a hermetically sealed body. A configuration of this type of the mixing and application capsule according to the invention is particularly advantageous as the components, capsule body, first and second plunger body can be configured identically for a large number of different liquid capsules. Different liquid capsules may have different liquids or different liquid quantities.

The second plunger body is preferably configured as a liquid capsule. This embodiment is particularly advantageous as capsule bodies and first plunger bodies can be configured as standard components thus enabling production which is advantageous in terms of time and cost. The second plunger body may be configured differently for different mixing purposes, i.e. it may, for example, have different liquids or different liquid quantities.

The liquid capsule is preferably sealed with a foil. The liquid capsule is particularly preferably hermetically sealed with an easily tearable foil. This is particularly advantageous to already allow an opening of the liquid capsule even with light pressure on the second plunger body.

The foil preferably has at least one layer, which is at least partly a metal layer. It is preferable if the foil is impermeable to gas. A central region of the foil preferably has a metal layer. The metal layer preferably consists of a hard, easily tearable aluminum. A radial region of the foil preferably has a metal layer. The foil is preferably sealably coated on at least one side. The sealing layer preferably has a heat-seal lacquer. These embodiments used in a combined manner or alternatively have the advantage that the foil is used as a liquid barrier in particular to a component in the mixing chamber. In particular, an evaporation through the foil can be particularly effectively avoided in this manner.

The liquid capsule preferably at least partly has metal. Metal is advantageously used as an evaporation and volatilization barrier for the liquid. It is therefore preferred for the liquid capsule to be manufactured at least partially from metal. Furthermore, the inner layer is preferably also sealably coated, for example with a heat-seal lacquer. Other barrier layer materials or multi-layer upper structures with at least one barrier layer are also conceivable. Depending on the liquid used, possible examples as barrier layers are polyvinyl alcohol, ceramic fillers or other materials, which the person skilled in the art will accordingly choose for the purpose.

The mixing and application capsule, in particular the first plunger body, has a resistor element for the controlled prevention of displacement of the first plunger body into the capsule body. The displacement of the first plunger body is preferably controlled in such a way that the displacement of the first plunger body is only possible when the projection of the first plunger body is introduced into the cavity of the second plunger body or is introduced so far into the cavity of the second plunger body that the cavity is emptied. The resistor element is preferably realized in that the external diameter of the plunger body is at least partially larger than the internal diameter of the capsule body. An arrangement of this type advantageously means that the first plunger body cannot be inserted into the capsule body unintentionally. It is preferred for the larger external diameter to be configured by at least one tab, the tab preferably projecting from the capsule body. It is also preferred for the tab to engage in an annular groove in the interior of the capsule body. The first capsule body preferably has a tab rim at the end which receives the second plunger body. The tab rim preferably has radially outwardly bent tabs, or radially outwardly projecting tabs and tabs oriented parallel to the longitudinal axis of the first plunger body. On activation of the mixing and application capsule according to the invention, by applying a first force, the second plunger body is pushed into the first plunger body. A second force is preferably necessary to bend the tab and release or allow the displaceability of the first plunger body, the second force preferably being greater than the first force. Particularly preferably, the capsule body has an annular notch, in order to receive the tab or the tabs. Particularly preferably, the second plunger body, at its end which projects from the capsule body, has an indentation, which receives the tab, so a displacement of the first plunger body is only released if the tab is latched in the indentation, i.e. the second plunger body is introduced, in particular completely, into the first plunger body. A mixing and application capsule according to the invention is particularly preferably configured according to the invention in such a way that the first plunger body is configured as a sleeve for receiving the second plunger body, the first plunger body has radially outwardly bent tabs projecting out of the capsule body at the end which receives the second plunger body, the second plunger body has an indentation, the indentation is configured as an annular gap, and the tabs and annular gap are configured as a pairing in such a way that the displacement of the first plunger body is not possible until the tab is arranged in the annular gap. It is advantageously thus ensured that the liquid in the cavity of the second plunger body is completely pushed out therefrom in a first step before the dental compound produced is discharged in a further step.

A further preferred configuration to prevent the unintentional displacement of the first plunger body during activation, i.e. during the pressing out of the liquid, is the provision of correspondingly expediently selected friction conditions.

The capsule body preferably has a venting device for removing a gas from the mixing chamber of the capsule body. A venting device of this type is preferably configured as a gas-permeable filter membrane, which is impermeable to the mixing component in the mixing chamber and is arranged in at least a part of the outer wall of the plunger body. A filter membrane of this type is described, for example, in US 2004/0104133 A1, the disclosed filter membrane of which is referred to here. It is furthermore preferred for the seal between the capsule body and first plunger body to have venting slots. The venting slots are preferably arranged on the outer surface of the first plunger body and interrupt an annular sealing element of the first plunger body. Such configurations are preferred as the air in the interior of the capsule body can be removed particularly rapidly, so entry of the liquid into the mixing chamber is facilitated. This slotted seal is preferably configured several times one behind the other, the slots being offset with respect to one another, so a type of labyrinth seal is produced.

The projection of the first plunger body is preferably configured to open the liquid capsule. It is preferred for the projection of the first plunger body to be configured to puncture, push open, cut open, break open, and/or punch open the foil. This embodiment of the mixing and application capsule according to the invention is advantageous as an opening of the liquid capsule and a pressing out of the liquid is achieved in one movement in the method step of pressing the second plunger body into the first plunger body.

The projection of the first plunger body preferably has means for punching out a region of the foil, which opposes the channel. By means of this embodiment of the mixing and application capsule according to the invention it is particularly advantageously achieved that only the relevant region of the foil for transferring the liquid from the cavity into the mixing chamber, namely that which opposes the channel, is opened. A loss of liquid in the radial direction is thus avoided.

A mixing and application capsule for producing a dental preparation is particularly preferred which has: a capsule body with a mixing chamber for receiving a mixing component and for mixing the dental preparation from the mixing component and a fluid and with an outlet opening for discharging the dental preparation, a first plunger body which can be displaced in the capsule body, delimits the mixing chamber in the capsule body and has a channel to guide the fluid from a cavity into the mixing chamber and a projection, and a second plunger body which can be displaced in the capsule body and has the cavity to receive the fluid, the cavity being configured to receive the projection of the first plunger body, wherein the mixing and application capsule also has a cannula pivoting element at the outlet opening for applying the dental preparation, the capsule body having a gas-permeable filter membrane and/or the seal between the capsule body and first plunger body having venting slots for removing a gas from the mixing chamber of the capsule body, the second plunger body being configured as a liquid capsule and the liquid capsule being sealed with an aluminum foil, the aluminum foil being sealably coated on at least one side, the first plunger body having at least one tab rim with radially outwardly bent tabs projecting out of the capsule body and the second plunger body having an indentation at its end projecting out of the capsule body, the indentation being configured to receive the bent tabs, the first plunger body having an edge recess, which is configured to receive an edge projection of the second plunger body, and wherein the projection of the first plunger body has pins for punching out a region of the foil, which opposes the channel.

As an alternative to the cannula pivoting element shown here, another opening mechanism is conceivable, for example, as described, for example, in DE19906887C1.

The projection of the first plunger body preferably has a blade for cutting open the foil, the blade being arranged along the periphery of the projection. The projection of the first plunger body preferably has elevations extending radially from the channel to the blade to assist the outflow of the liquid into the channel. Such configurations of the mixing and application capsule according to the invention offer the advantage that a long region of the foil is simultaneously cut open and the liquid can be rapidly removed from the cavity through the channel. The risk of a loss of liquid is thus avoided.

A mixing and application capsule according to the invention for producing a dental preparation is particularly preferred which has: a capsule body with a mixing chamber for receiving a mixing component and for mixing the dental preparation from the mixing component and a fluid and with an outlet opening for discharging the dental preparation, a first plunger body which can be displaced in the capsule body, delimits the mixing chamber in the capsule body and has a channel to guide the fluid from a cavity into the mixing chamber and a projection, and a second plunger body which can be displaced in the capsule body and has the cavity to receive the fluid, the cavity being configured to receive the projection of the first plunger body, wherein the mixing and application capsule also has a cannula pivoting element at the outlet opening for applying the dental preparation, the capsule body having a gas-permeable filter membrane and/or the seal between the capsule body and first plunger body having venting slots for removing a gas from the mixing chamber of the capsule body, the second plunger body being configured as a liquid capsule and the liquid capsule being sealed with an aluminum foil, the aluminum foil being sealably coated on at least one side, the first plunger body having at least one tab rim with radially outwardly bent tabs projecting out of the capsule body and the second plunger body having an indentation at its end projecting out of the capsule body, the indentation being configured to receive the bent tabs, the first plunger body having an edge recess, which is configured to receive an edge projection of the second plunger body, and wherein the projection of the first plunger body has a blade for cutting open the foil and elevations extending radially from the channel to the blade, the blade being arranged along the periphery of the projection.

The second plunger body preferably has a projection in order to open the liquid capsule. The projection of the second plunger body is preferably conical. The projection of the second plunger body is preferably configured to puncture, push open, cut open, break open and/or punch open the foil. The projection of the first plunger body and the projection of the second plunger body are preferably configured to open the foil by the action of force on both sides. An arrangement of this type provides the advantage that the liquid capsule is opened in the direction in which the liquid has to flow in order to enter the mixing chamber. Owing to the movement of the projection of the second plunger body in the direction of the mixing chamber, the movement of the fluid is correspondingly initiated, whereby liquid losses are further avoided.

A further advantage of this configuration is that the liquid channel of the first plunger body on complete displacement of the second plunger body is filled by the projection of the second plunger body and the liquid quantity possibly remaining in the liquid channel is significantly reduced.

It is to be regarded as a further advantage that the liquid channel, from this aspect, may have larger dimensions without the liquid quantity remaining in the channel being increased. This, in particular, provides advantages if the first plunger is produced as an injection-molded part, because very small and, in relation to the diameter, very long channels, bring about premature tool wear. The process reliability in the production of the first plunger body is correspondingly higher.

The projection of the first and/or second plunger body is preferably configured to open the liquid capsule, in particular to puncture it. If projections of both the first and the second plunger body are used to open the liquid capsule, this provides the advantage that a particularly reliable and rapid opening is made possible and a particularly rapid outflow of the liquid through the channel into the mixing chamber can be achieved. Liquid losses in the radial direction can thus be avoided. Furthermore, with a puncturing of the liquid capsule, a very targeted opening process is achieved, so it can be established very precisely by the producer where the liquid capsule is to be punctured to ensure a rapid and loss-free outflow of the liquid into the mixing chamber.

The channel is preferably configured to receive the projection of the second plunger body. An arrangement of this type is particularly advantageous as the projection of the second plunger body, by introduction into the channel, ensures that no liquid residues remain in the channel. A precise mixing ratio of the fluid and component in the mixing chamber can thus be better adjusted. Furthermore, a simple manufacturing of the first plunger body by the injection-molding method is made possible as the channel is already inserted during the injection-molding production and does not have to be drilled in retrospectively.

A mixing and application capsule according to the invention for producing a dental preparation is particularly preferred which has: a capsule body with a mixing chamber for receiving a mixing component and for mixing the dental preparation from the mixing component and a fluid and with an outlet opening for discharging the dental preparation, a first plunger body which can be displaced in the capsule body, delimits the mixing chamber in the capsule body and has a channel to guide the fluid from a cavity into the mixing chamber and a projection, and a second plunger body which can be displaced in the capsule body and has the cavity to receive the fluid, the cavity being configured to receive the projection of the first plunger body, wherein the mixing and application capsule also has a cannula pivoting element at the outlet opening for applying the dental preparation, the capsule body having a gas-permeable filter membrane and/or the seal between the capsule body and first plunger body having venting slots for removing a gas from the mixing chamber of the capsule body, the second plunger body being configured as a liquid capsule and the liquid capsule being sealed with an aluminum foil, the aluminum foil being sealably coated on at least one side, the first plunger body having at least one tab rim with radially outwardly bent tabs projecting out of the capsule body and the second plunger body having an indentation at its end projecting out of the capsule body, the indentation being configured to receive the bent tabs, wherein the first plunger body has an edge recess configured to receive an edge projection of the second plunger body, wherein the second plunger body has a conical projection in order to puncture, push open, cut open, break open, and/or punch open the liquid capsule, and the channel being configured to receive the conical projection of the second plunger body. It is particularly preferred in this embodiment that the projection of the first plunger body and the projection of the second plunger body are configured and cooperate with one another to open the foil by the action of force on both sides.

The first plunger body preferably has an edge recess, which is configured to receive an edge projection of the second plunger body. The edge recess is preferably configured to guide the edge projection. The edge recess and edge projection preferably form a seal between the cavity and an outer region of the mixing and application capsule. An embodiment of this type of the mixing and application capsule according to the invention provides the advantage that a volatilization of the fluid in the edge regions of the first and second plunger body can be further reduced. Furthermore, this provides the advantage that mechanical guidance of the second plunger body is provided during the introduction into the first plunger body.

The second plunger body preferably has a peripheral projection, which is configured as a protrusion, and which, on the one hand, is used as a seal between the first and second plunger and, on the other hand, together with a shoulder, in particular in the interior of the first plunger body, means that the second plunger body does not unintentionally slide out during storage and transportation.

A mixing and application capsule according to the invention for producing a dental preparation is particularly preferred, which has: a capsule body with a mixing chamber for receiving a mixing component and for mixing the dental preparation from the mixing component and a fluid and with an outlet opening for discharging the dental preparation, a first plunger body which can be displaced in the capsule body, delimits the mixing chamber in the capsule body and has a channel to guide the fluid from a cavity into the mixing chamber and a projection, and a second plunger body which can be displaced in the capsule body and has the cavity to receive the fluid, the cavity being configured to receive the projection of the first plunger body, wherein the mixing and application capsule also has a cannula pivoting element at the outlet opening for applying the dental preparation, the capsule body having a gas-permeable filter membrane and/or the seal between the capsule body and first plunger body having venting slots for removing a gas from the mixing chamber of the capsule body, the second plunger body having a liquid capsule and the liquid capsule being sealed with an aluminum foil, the aluminum foil being sealably coated on at least one side, the first plunger body having at least one tab rim with radially outwardly bent tabs projecting out of the capsule body and the second plunger body having an indentation at its end projecting out of the capsule body, the indentation being configured to receive the bent tabs, the first plunger body having an edge recess, which is configured to receive an edge projection of the second plunger body, and wherein the projection of the first plunger body is convex or rounded or hemispherical and the base of the liquid capsule, i.e. the wall of the liquid capsule opposing the foil, is concave or rounded or hemispherical.

It is further preferred that the capsule body, first, second plunger body and/or the liquid capsule are cylindrical. It is particularly preferred for their elements, in particular recesses, projections, cavity, liquid capsule, resistor element, venting device, means for punching out and/or blade, as described above in detail are configured and/or arranged rotationally symmetrically.

The channel is preferably arranged parallel to the longitudinal axis of the first plunger body. The channel is preferably also arranged in the centre of the first plunger body. It is further preferred for the channel to be arranged in an edge region of the first plunger body. It is particularly preferred for the channel to have means for preventing discharge of the mixing component. A means of this type is preferably arranged at the end of the channel facing the mixing chamber. The means is also preferably a tapering in the interior of the channel.

It is also preferred for the mixing and application capsule according to the invention to have a cannula pivoting element, which is coupled to the outlet opening, in order to apply the dental preparation.

The channel preferably has means to prevent the mixing component from the mixing chamber entering the channel. These means particularly preferably prevent undesired entry of the mixing component into the channel. It is furthermore preferred that a means of this type is arranged between the first plunger body and the capsule body, for example as a foil, which separates the mixing chamber from the first capsule body. It is preferred in particular for the means for preventing the entry of the mixing component from the mixing chamber into the channel to be a check valve, a flexible check flap, a porous structure, a narrow gap and/or a membrane which can be torn open. With a configuration of this type it is advantageously achieved that the first mixing component, in particular the powder component, remains in the mixing chamber until activation by mixing with the fluid, or is protected from outer influences, and the desired mixing ratio determined by the producer coincides as well as possible with the actual mixing ratio in fact achieved in the mixing chamber.

The outlet opening preferably has a cannula, which has means on its inside for arranging an extension. It is preferred, in particular, for the outlet opening and/or the cannula to have means which allow an attachment of a thin extension, in particular. The cannula is preferably straight or (optionally partially) bent. It is preferred for the cannula to have, on its inside, devices which allow the attachment or insertion of a separate very thin extension. This extension may, for example, latch in non-detachably by means of a snap-on mechanism or be held by friction. Such extensions are used, for example, for root canal fillings, but tend to be a hindrance during activation or mixing, because they are mechanically sensitive. For this reason, it is recommended to attach an extension of this type only after mixing.

The outlet opening of a mixing and application capsule according to the invention is preferably configured for connection to a cannula (or another device for discharging the dental preparation), i.e. it does not have a cannula. A modular construction of this type is advantageous as the cannula (and optionally the thin extension) can be selected individually depending on the purpose and site of use.

BRIEF DESCRIPTION OF THE DRAWINGS

The invention will be described in more detail below for better understanding with the aid of some embodiments, in which.

DETAILED DESCRIPTION

Figure 1:
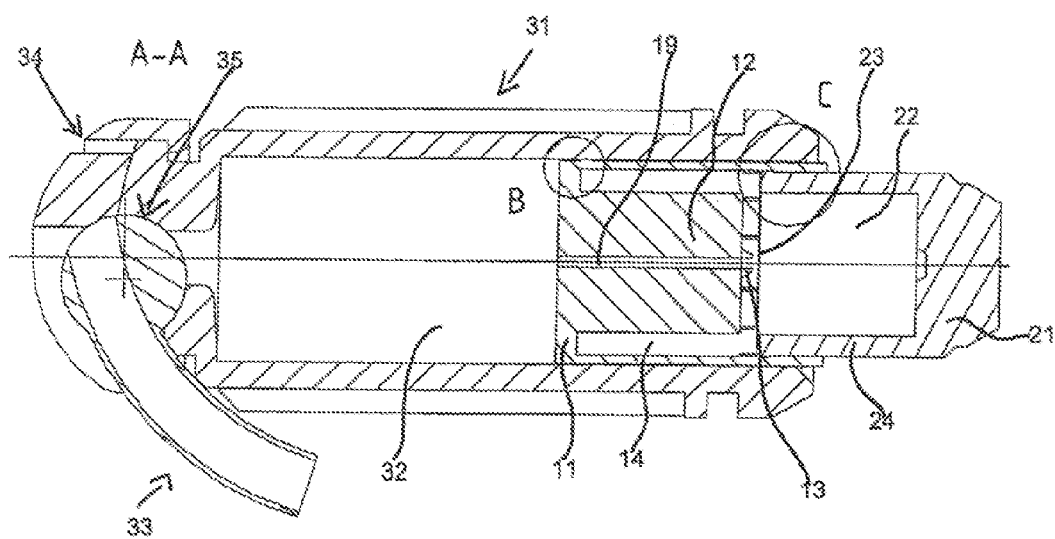
FIG. 1 shows an embodiment of a mixing and application capsule according to the invention.

FIG. 1 illustrates an embodiment of a mixing and application capsule for producing a dental preparation 43 with a capsule body 31, a first plunger body 11 configured as a passage plunger and a second plunger body 21 configured as a liquid container. The capsule body 31 is substantially cylindrical and has, at its first end, a cap 34, on which a cannula 33 is rotatably arranged by means of an articulated joint 35. The cannula joint arrangement 33, 35 is preferably configured as a cannula pivoting element. In a first position (as shown in FIGS. 1 and 2a to 2c), the cap 34 and the cannula 33 are rotated by means of the articulated joint 35 in such a way that the inside of the cannula 33 is not connected to the mixing chamber 32 of the capsule body 31. In a second position, the cap 34 and cannula 33 are arranged by means of the articulated joint 35 (as explained below with reference to FIG. 2d) in such a way that the dental compound 43 mixed in the interior of the capsule body 31 can be discharged through the cannula 33.

Arranged in the interior of the capsule body 31 is the mixing chamber 32, which is configured as a cavity and, in the filled state of the mixing and application capsule, has a powdery component 41, which, mixed with liquid 42, forms the dental preparation 43. The mixing chamber 32 is delimited at the first end of the capsule body 31 by the cap and cannula arrangement 33, 34 and, at the second end, configured to be open, of the capsule body 31 is delimited by the passage plunger 11. Moreover, the component 41 may not only be powdery, but instead may also be paste-like, liquid or fluid.

The passage plunger 11 is displaceably arranged along the longitudinal axis of the capsule body 31. It is used for pressing out the dental compound produced in the mixing chamber 32 through the cannula 33. The passage plunger 11 has a channel 19 for guiding a fluid 42, which is configured as a through-channel. A fluid in the sense of this application is a substance, which does not oppose a sheer stress however small with any resistance, as applies, in particular, to gases and liquids. In the embodiment shown in FIG. 1, the through-channel 19 is configured along the central longitudinal axis of the passage plunger 11. The through-channel 19 forms the connection between the mixing chamber 32 and the second plunger body 21, which has a cavity 22 to receive the fluid 42. The through-channel 19 is configured to prevent the powdery component 42 entering the channel or passing through it. The channel 19 may have corresponding means or be configured correspondingly narrow.

Such means for preventing powder entering the channel may, for example, be a sponge-like, porous mass or a check flap or a check valve or a thin membrane, which tears open during activation.

The second plunger body configured as a liquid container 21 is arranged on the side of the passage plunger 11 remote from the mixing chamber 32. The liquid container 21 has an, in particular, sealable or sealably coated cavity 22, in which the liquid 42 is arranged, which is used for mixing the dental preparation 43 in combination with the powdery component 41. The cavity 22 of the liquid container 21 is hermetically sealed by a foil 23. The foil 23 is preferably an aluminum foil, which is sealably coated on at least one side. The sealing layer preferably consists of a heat-sealing lacquer, but may also be a laminate layer.

The passage plunger 11 has a projection 12 as a ram, which, with regard to the form and/or the volume corresponds to the cavity 22. The projection 12 has at least one pin 13, which is used to cut open or punch out the foil 23 of the liquid container 21.

The cavity 22 of the liquid container 21 is delimited laterally by a radial projection or edge projection 24, which forms the edge region of the liquid container 21 and the side wall of the cavity 22. The edge projection 24 is used to guide the liquid container 21 during displacement along the longitudinal axis of the capsule body 31 and is received in a correspondingly formed edge recess 14 in the edge region of the passage plunger 11.

A liquid loss from the liquid container 21 is avoided according to the invention as three sides of the liquid container 21 are so thick-walled that a liquid loss through the walls does not occur. A liquid loss through the relatively thin-walled foil 23 is prevented by the foil 23 being manufactured at least partially from metal. In the case, a layer of the foil 23 is, for example, configured as a metal layer and/or specific regions of the foil 23 have a metal fraction. The liquid 42 may, according to the invention, be stored in this manner over a long time period in the cavity 22, without risking evaporation of the liquid or other volatilization.

Since virtually no liquid can escape from the cavity 22, the purity of hygroscopic powder 41 in the mixing chamber 32 also remains guaranteed over a long time period. A mixing and application capsule is generally stored in a hermetically sealed receptacle, such as a blister or a tubular pouch. According to the invention, a long storability of the mixing and application capsule is achieved.

The dental preparation 43 mixed from the powdery and the liquid component 41, 42 has properties which are precisely adjusted by the producer, as virtually no liquid residues remain in the cavity 22 when the cavity 22 is pushed over the projection 12. As no sliding seal delimits the fluid 42 of the mixing and application capsule according to the invention, a liquid loss via a seal of this type can also be avoided and the sliding seals between the liquid container 21 and passage plunger 11 and between the passage plunger 11 and capsule body 31 can be configured to be correspondingly smooth-running as they are only used at the moment of activation and therefore are not in contact with liquid during storage. It is possible to activate the capsule with a low application of force.

It is also possible to accommodate a large liquid quantity in a liquid container 21, which in a case such as this is configured correspondingly long (and analogously with this, the projection 12 of the passage plunger 11), without the diameter of the mixing and application capsule having to be enlarged, which would lead to a non-manageability during application in the oral cavity of the patient. As the activation and the discharge of the dental preparation 43 takes place by the application of force in only one direction, i.e. along the longitudinal axis of the mixing and application capsule, the use of the mixing and application capsule according to the invention is possible with the aid of only one tool and in a particularly simple manner and in a short time.

The operation of the mixing and application capsule according to the embodiment shown in FIG. 1 by activation and discharge of the dental preparation is shown in FIGS. 2a to 2d. The mixing and application capsule of FIGS. 2a to 2d has the capsule body 31, the passage plunger 11 and the liquid container 21. A liquid 42 is arranged in the cavity 22 of the liquid container 21, the cavity 22 being sealed by a foil 23. The powder 41 is arranged in the mixing chamber 32 of the capsule body 31, which is delimited, on the one hand, by the flap and cannula arrangement 33, 34 and, on the other hand, the passage plunger 11.

Figure 2A:
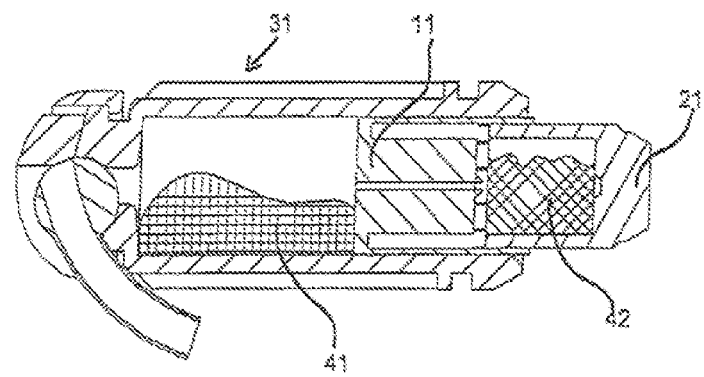
FIGS. 2a to 2d show the operation of the mixing and application capsule of FIG. 1.
Figure 2B:
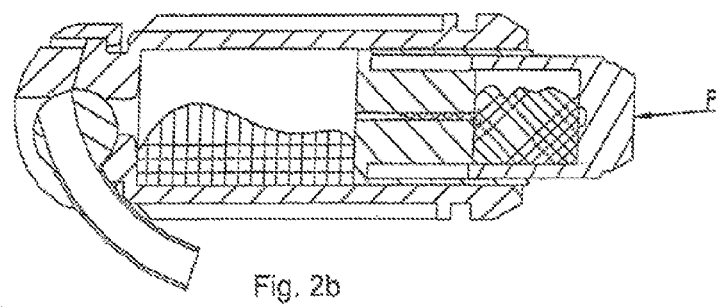
Figure 2C:
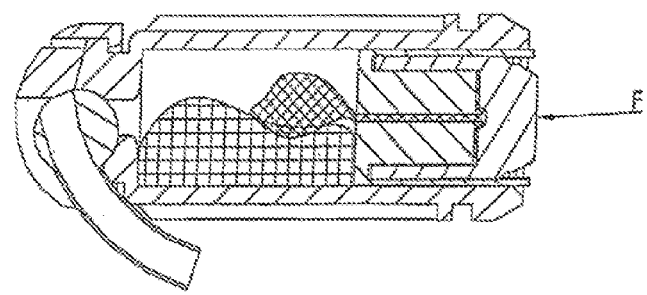

The operation of the mixing and application capsule according to the invention will now be described starting with FIG. 2a. FIG. 2a shows the starting situation described above.

In a first method step (FIG. 2b), pressure is exerted on the liquid container 21 in the direction of the passage plunger 11 along the longitudinal axis of the capsule body 31. By bringing pins 13 of the projection 12 of the passage plunger 11 into contact with the foil 23 of the liquid container 21, the pins 13 pierce the foil 23 and, on further displacement of the liquid container 21, punch out a part region of the foil 23. The liquid cavity 22 is opened. As the pins 13 are arranged close to the through-channel 19, the liquid 42 flows off directly through the through-channel 19 into the mixing chamber 32 of the plunger body 31.

By further displacement of the liquid container 21 in the direction of the passage plunger 11, the projection 12 of the passage plunger 11 is introduced into the cavity 22 of the liquid container 21, it displaces the liquid 42 out of the cavity 22 and pushes it into the through-channel 19 and the mixing chamber 32 of the capsule body 31. Since the liquid container 21 is laterally delimited by the edge region 24, which is introduced in recesses 19 in the passage plunger 11, a liquid loss in the edge region and via the seal between the passage plunger 11 and the liquid container 5 can be avoided. It is of assistance here that the single escape possibility for the air located in the edge recess 14 is provided through the channel 19 and this air entrains the liquid 42 with it. The air thus introduced into the mixing chamber and the air, which is displaced by the entering liquid 42 escape through the venting devices of the first plunger and/or the venting device of the capsule body.

If the projection 12 is completely introduced into the cavity 22, in which the liquid 42 was situated in the starting position, the first method step ends. The liquid quantity provided by the producer is now located in the mixing chamber 32 of the capsule body 31. The mixing then takes place in a mixing apparatus. These mixing apparatuses are generally conventional in the dental practice and give the capsule an intense shaking movement, which is frequently directed substantially parallel to the longitudinal axis of the capsule. The capsule is clamped for this purpose in a receiving fork and held tight by a spring force. The clamping points are the cap 34 and liquid container 21. This means that, in each case, in the reversing position of the shaking movement, in each case, apart from the spring force of the receiving fork, an acceleration force also acts on the liquid container 21 and any incomplete liquid emptying during mixing is further improved. Depending on the type of receiving fork and the mixing apparatus, it is moreover possible for the activation to take place during the clamping and/or during the mixing. Manual activation can in this case be dispensed with.

Figure 2D:
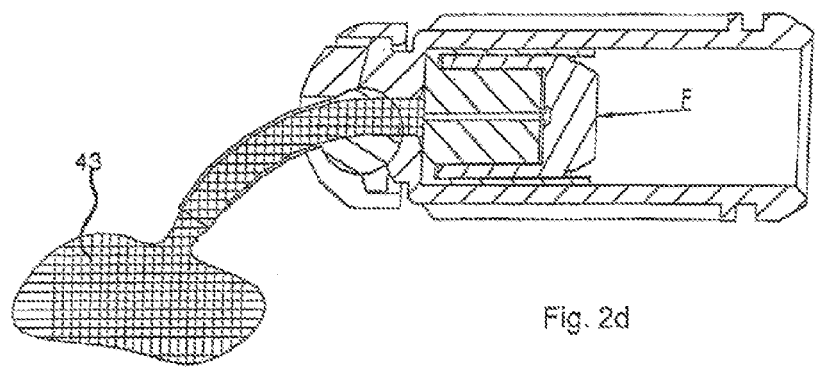

The next method step for using the mixing and application capsule if used to discharge the mixed paste 43 (FIG. 2d). For this purpose, the articulated joint 35 is brought into the second position, so the cannula 33 forms a connection between the mixing chamber 32 and outer region of the mixing and application capsule. By exerting further pressure on the liquid container 21, the liquid container 21, and simultaneously the passage plunger 11, are displaced in the direction of the mixing chamber 32 and the volume thereof is reduced. Simultaneously, the mixing chamber 32 is further vented by means of the venting device of the capsule body 31 or passage plunger 11 if the air does not discharge from the cannula. The mixed paste 43 is then discharged through the cannula 33 and can be applied.

Figure 3A:
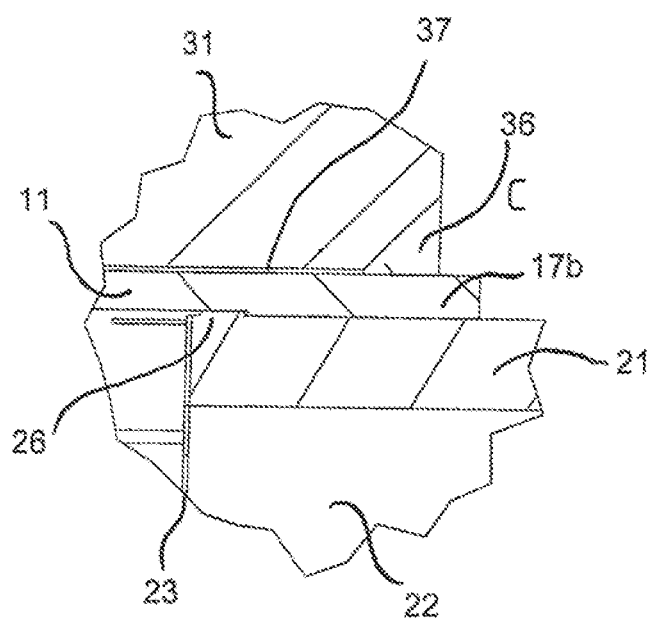
FIGS. 3a to 3e show detailed views of the mixing and application capsule of FIG. 1.

FIG. 3a shows a detailed view of the region C of FIG. 1, in which the region between the liquid container 21, passage plunger 11 and capsule body 31 is shown. The notch 36 is used here to receive a radially outwardly bent tab 17a between the capsule body 31 and passage plunger 11, as will be described below. As is shown in FIG. 3a, the liquid container 21 has a protrusion 26, which strikes against a step of the interior of the passage plunger 11 in such a way that the liquid container 21 is prevented from sliding out of the passage plunger 11. Furthermore, the step and protrusion arrangement can be used to prevent a discharge of liquid when the foil 23 is opened and the liquid flows out of the cavity 22.

Figure 3B:
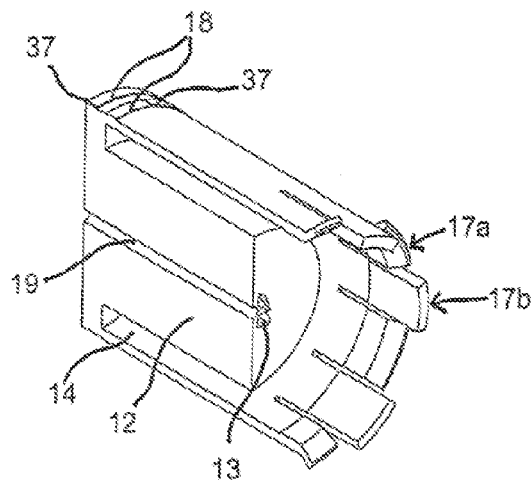

FIG. 3b shows a semi-cut-open detailed view of the passage plunger 11. The passage plunger 11 according to the embodiment shown in FIG. 1 has a through-channel 19, which is located in the centre of the projection 12. Furthermore, two or four pins 13 are shown in FIG. 3b, which are used to punch out a central region of the foil 23 of the liquid container 21. FIG. 3b also shows a tab rim, which is used as a resistor element in order to ensure the two-step operation described in regard to FIGS. 2a to 2d, i.e. the activation and discharge. The tab rim has radially outwardly bent tabs 17a and tabs 17b configured parallel to the longitudinal axis of the passage plunger 11.

Figure 3C:
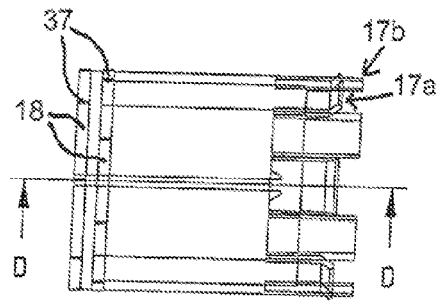
Figure 3D:
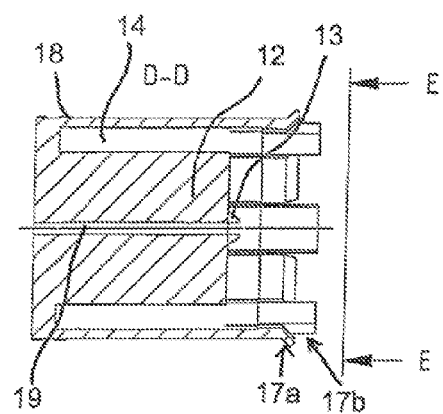
Figure 3E:
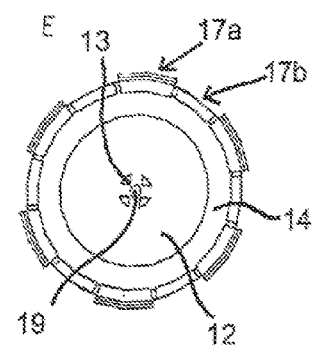

FIGS. 3c to 3e show further detailed views of the passage plunger 11 of FIG. 1 according to the axes shown.

Figure 4:
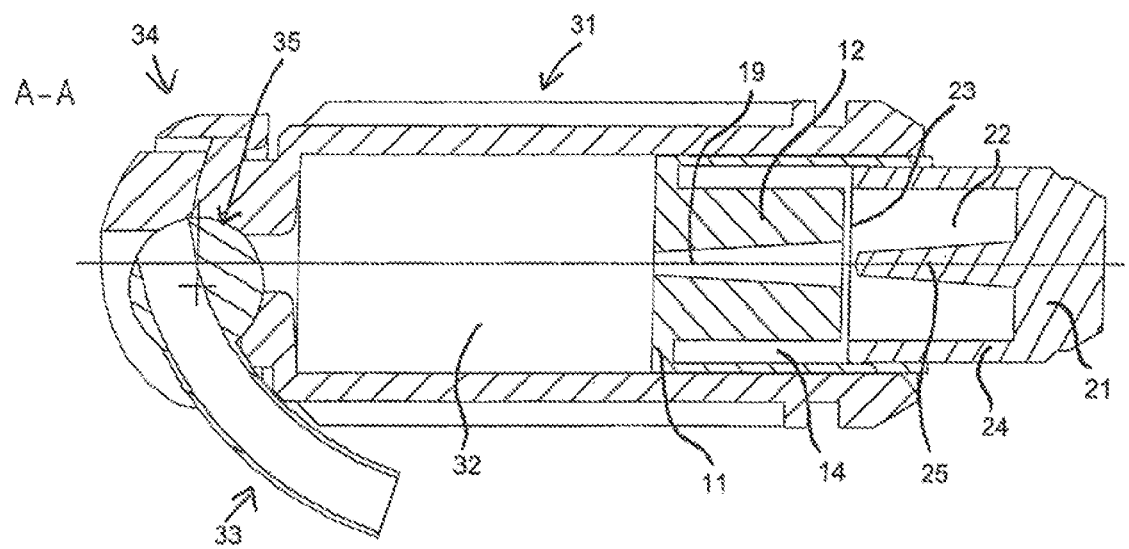
FIG. 4 shows a further embodiment of a mixing and application capsule according to the invention.

FIG. 4 shows a further embodiment of the mixing and application capsule according to the invention. Statements and descriptions for components, which have already been described above with the same reference numerals, apply analogously below.

The embodiment shown in FIG. 4 differs from the embodiment of FIG. 1 by the configuration of the passage plunger 11 and liquid container 21. The liquid container 21 has, in its interior, a projection, which is configured as a pin 25. The pin 25, with regard to the configuration and/or volume, substantially corresponds to the through-channel 19 of the passage plunger 11. The through-channel 19 of the passage plunger 11 is conical in the embodiment of FIG. 4 in order to receive the pin 22. Other cross sections, such as, for example, pyramid-shaped, cylindrical or star-shaped are also possible.

Figure 5A:
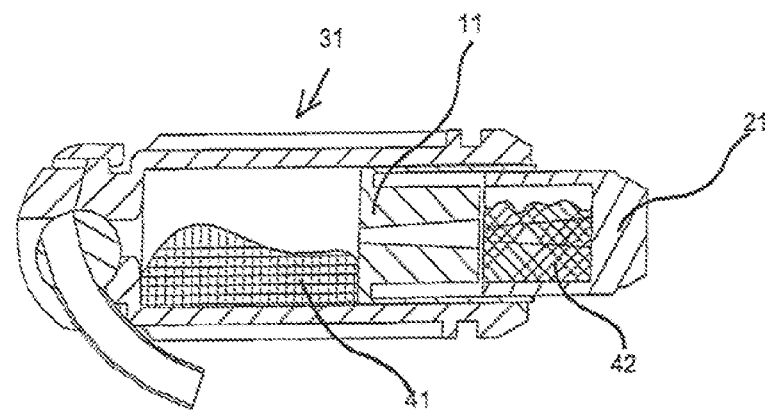
FIGS. 5a to 5d show the operation of the mixing and application capsule of FIG. 4.

FIGS. 5a to 5d show the activation of the mixing and application capsule of FIG. 4 and the discharge of the mixed paste 43 through the cannula 33. In this case, the sequence in FIGS. 5a to 5d differs from that of FIGS. 2a to 2d with regard to the activation of the mixing and application capsule. In FIG. 5a, the starting state is shown, in which a powder 41 is arranged in the mixing chamber of the plunger body 31, which has the passage plunger 11 in its interior, and the liquid container 21 is arranged on the side of the passage plunger 11 remote from the mixing chamber 32. The cavity 22 of the liquid container 21 has liquid 42 and is sealed with a foil 23. The pin 25 is arranged in the interior of the cavity 22 of the liquid container 21. By the application of force on the liquid container 21, the latter is pushed onto the passage plunger 11. The projection 12 of the passage plunger 11 acts as a resistance here, which opposes the foil 23 of the liquid container 21 and dents it in the centre in the direction of the cavity.

Figure 5B:
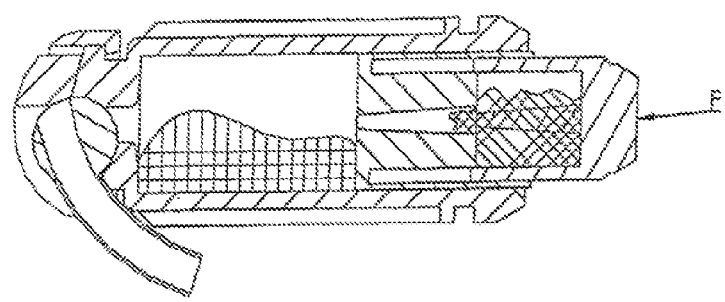
Figure 5C:
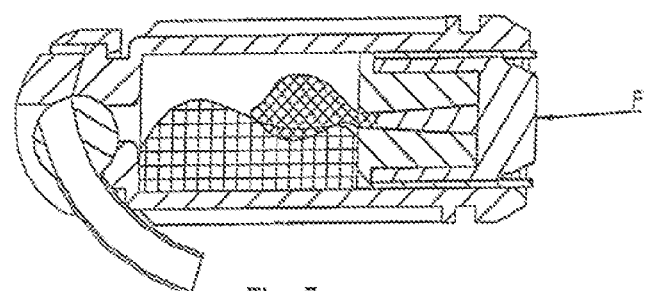
Figure 5D:
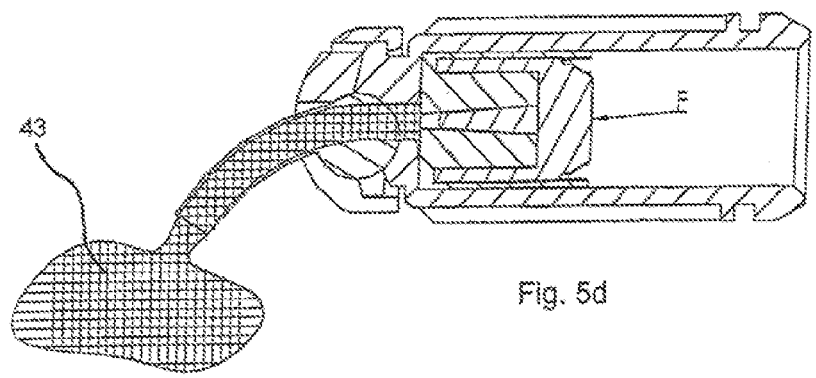

By exerting further pressure on the liquid container 21, the pin 25 opens or perforates the foil 23 in the region of the through-channel 19, as shown in FIG. 5b. The liquid can now discharge from the cavity 22 through the through-channel 19. By further insertion of the liquid container 21 into the passage plunger 11, the cavity 22 is taken up by the projection 12, so the cavity 22 is emptied of liquid. The pin 25 pushes the liquid through the through-channel 19 into the mixing chamber 32. A mixing of the powder 41 and the liquid 42 takes place in the mixing chamber 32, as described above, for example in a mixing apparatus and the mixed paste 43 can be discharged from the mixing and application capsule. Instead of powder 41, a liquid or pasty substance may alternatively be located in the mixing chamber 32 in this or another embodiment and is mixed with the liquid 42 with or without the aid of a mixing apparatus.

Figure 6:
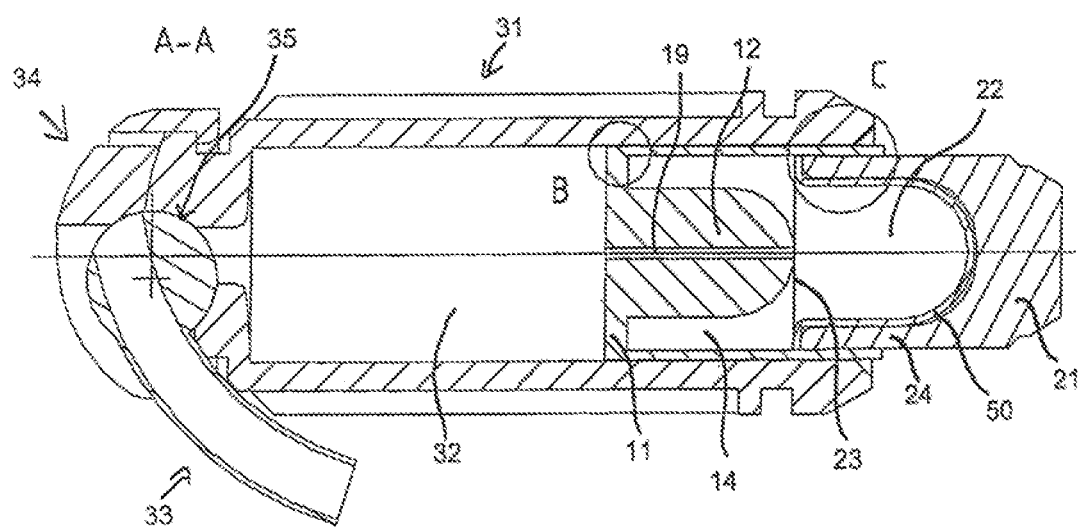
FIG. 6 shows a further embodiment of a mixing and application capsule according to the invention.
Figure 9:
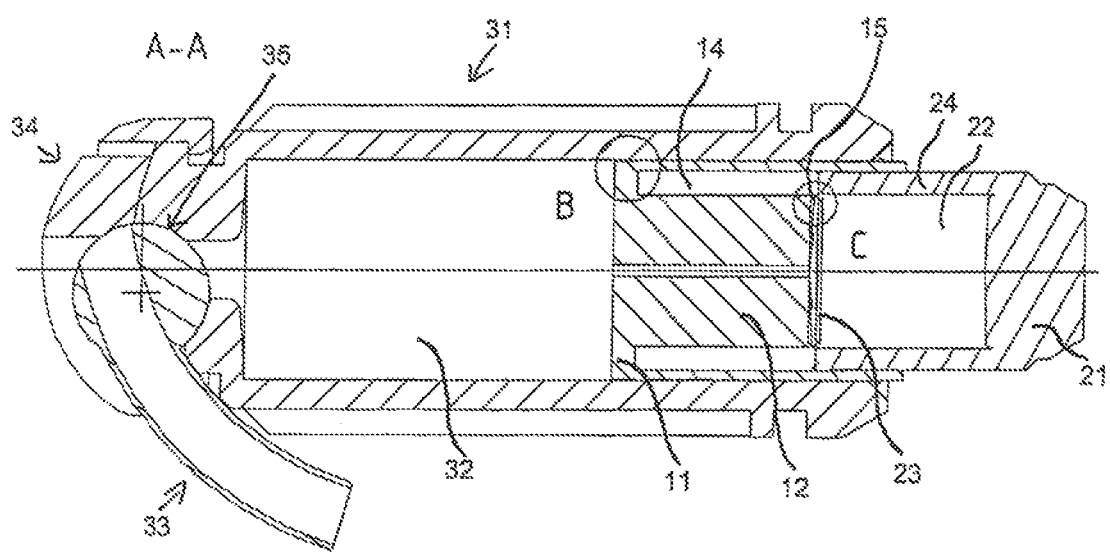
FIG. 9 shows a further embodiment of a mixing and application capsule according to the invention.

FIG. 6 shows a further embodiment of the mixing and application capsule according to the invention. The embodiment of FIG. 6 differs from those of FIGS. 1 and 4 with regard to the configuration of the passage plunger 11 and the liquid container 21. The liquid container 21 of the embodiment of FIG. 6 is configured to receive a liquid capsule 50. The interior of the liquid capsule 50 is preferably coated with sealing lacquer. In the embodiments of FIGS. 1, 4 and 9, the cavity 22 is configured as a liquid capsule integrated with the liquid container 21. It is, however, also possible for the embodiments of FIGS. 1, 4 and 9 to be equipped or operated with a separate liquid capsule 50. The liquid capsule 50 is hermetically sealed with a foil 23 relative to the projection 12 of the passage plunger 11. The liquid capsule 50 may consist here, for example, of a barrier material, such as, for example, aluminum, and has, on its inside, a sealable layer. Liquid losses through diffusion are completely ruled out in this embodiment (in particular virtually). The projection 12 of the passage plunger 11 is configured according to the embodiment of FIG. 6 with a round, convex hemispherical surface, so the opening of the foil 23 does not take place by means of a punching out or cutting open but by means of pushing open.

The advantage of the separate metallic liquid capsule is: the liquid capsule 50 can be produced economically by the deep-drawing method, whereas the container 21 with its comparatively complex geometry can be produced as an injection-molded part.

Compared with the prior art, as described, for example, in DE 3920537A1, the advantage is produced here that the liquid capsule 50 does not have to be deformed to empty the liquid, so it can have a substantially higher wall thickness and therefore can be deep-drawn substantially deeper in relation to the diameter. Furthermore, because of the deformation of the thick wall thickness of the liquid capsule 50, which does not take place during the activation, no folds can form, in which an unspecific quantity of liquid would remain.

Figure 7A:
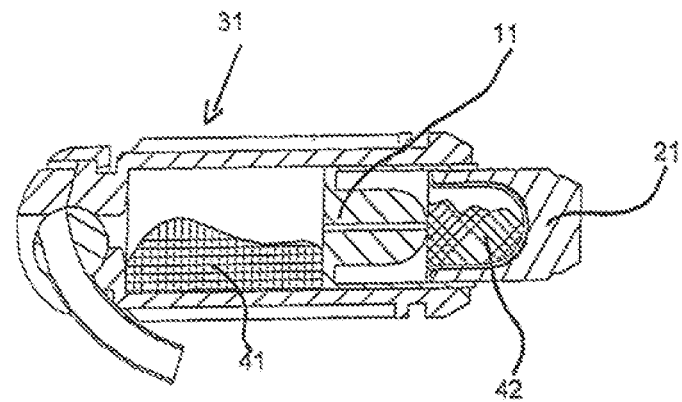
FIGS. 7a to 7d show the operation of the mixing and application capsule of FIG. 6.
Figure 7B:
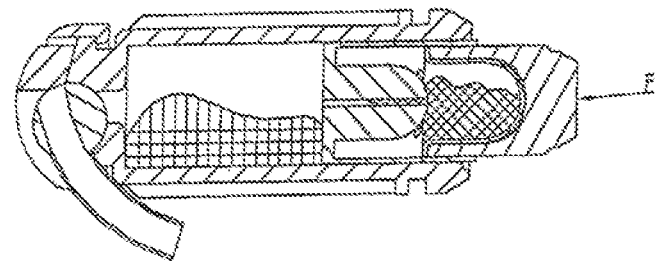
Figure 7C:
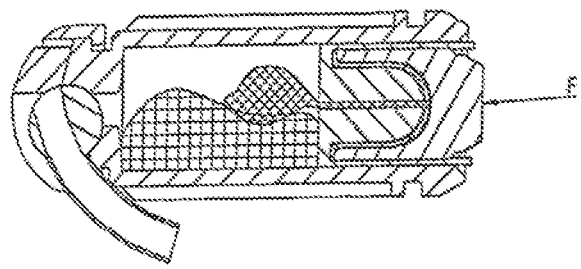
Figure 7D:
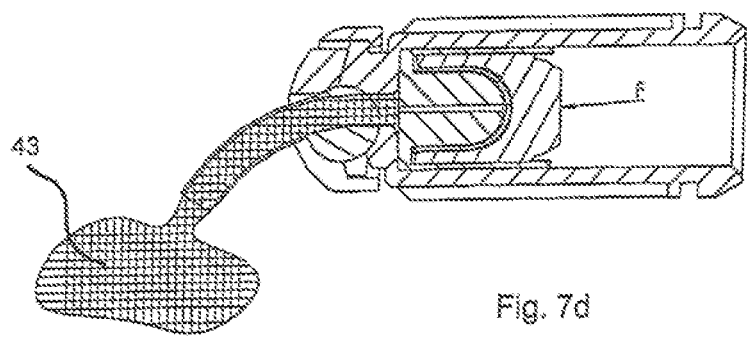

The activation of the mixing and application capsule of the embodiment of FIG. 6 and the discharge of the mixed paste 43 is shown in FIGS. 7a to 7d. In starting stage, the capsule body 31, passage plunger 11 and liquid container 21 with the liquid capsule 50 are in an arrangement as shown in FIG. 7a. The liquid 42 is arranged in the liquid capsule 50 and the powder 41 is arranged in the mixing chamber of the capsule body 31. By applying force onto the liquid container 21, the projection 12 of the passage plunger 11 breaks through the thin foil 23 and the liquid of the cavity 22 obtains access to the through-channel 19. The liquid runs the through the through-channel 19 and blends with the powder 41 in the mixing chamber 32. The projection 12 is completely pushed into the liquid capsule 50, so liquid residues from the cavity 22 of the liquid capsule 50 are pushed through to the concave hemispherically formed base thereof and pressed into the mixing chamber 32. After mixing the liquid 42 with the powder 41, pressure is exerted on the liquid container 21 and the passage plunger 11, so the mixed paste 43 discharges through the cannula 33.

Figure 8A:
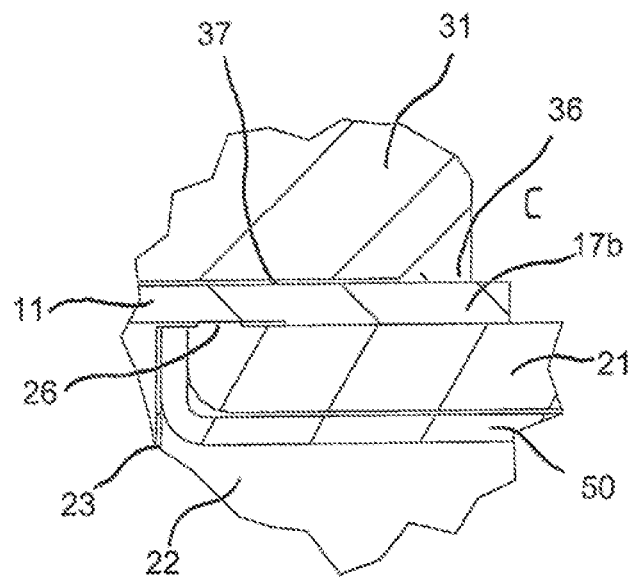
FIGS. 8a to 8e show detailed views of the mixing and application capsule of FIG. 6.

FIG. 8a is a detailed view of the region C of FIG. 6. Similarly to as shown in FIG. 3a, the liquid container 21 has an outer radial projection as a protrusion 26, which engages with a step of the passage plunger 11 to avoid the liquid container 21 sliding out and to achieve an additional sealing with respect to the edge recess 14. Also as in FIG. 3a, the capsule body 31 has an annular notch 36 to receive a resistor element 17a. It is also shown in FIG. 8a that the liquid capsule 50, which delimits the cavity 22, is inserted into the liquid container 21.

Figure 8B:
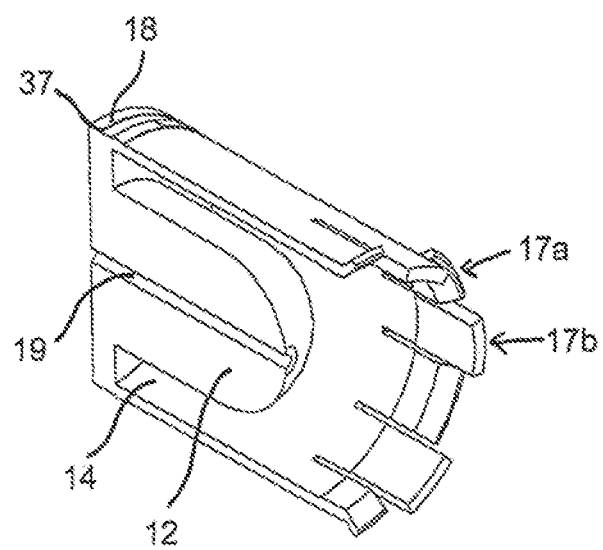
Figure 8C:
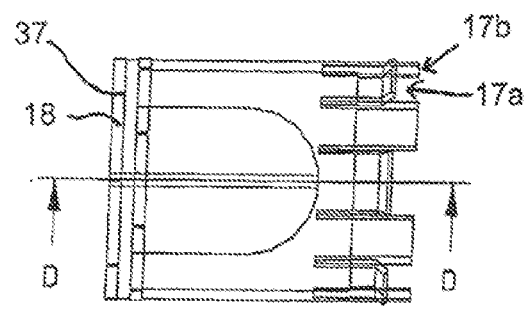
Figure 8D:
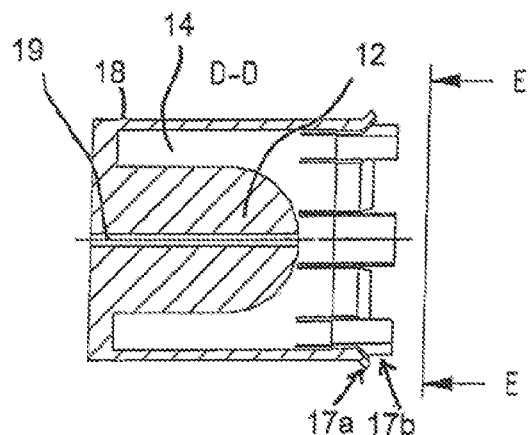
Figure 8E:
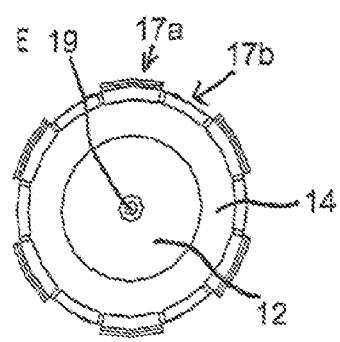

FIG. 8b shows a semi cut-open detailed view of the passage plunger 11 of the embodiment of FIG. 6. The projection 12 is provided here with a round, hemispherical surface, the through-channel 19 being arranged in the centre of the projection 12 along the longitudinal axis thereof. FIGS. 8c to 8e show further detailed views of the passage plunger 11 of FIG. 6 according to the axes shown.

FIG. 9 shows a further embodiment of the mixing and application capsule according to the invention. The embodiment of FIG. 9 differs from those of FIGS. 1, 4 and 6 with respect to the configuration of the passage plunger 11 and the liquid container 21. The projection 12 of the passage plunger 11 is cylindrical and has a blade 15 which extends along the periphery of the projection surface. Arranged on the surface of the projection 12 facing the foil 23 are also elevations 16, which extend in the radial direction between the through-channel 19 and blade 15.

The liquid container 21 is configured with a cylindrical cavity 22, which has recesses to receive the blade 15 and the elevations 16. The liquid container 21 is ram-like, i.e. configured with a corresponding profiling in order to receive the projection 12, blade 15 and elevations 16 in such a way that virtually no cavities remain between the passage plunger 11 and liquid container 21, in which liquid residues could remain.

Figure 10A:
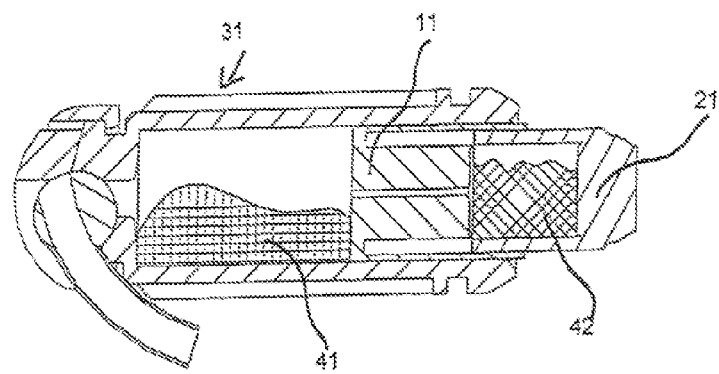
FIGS. 10a to 10d show the operation of the mixing and application capsule of FIG. 9.
Figure 10B:
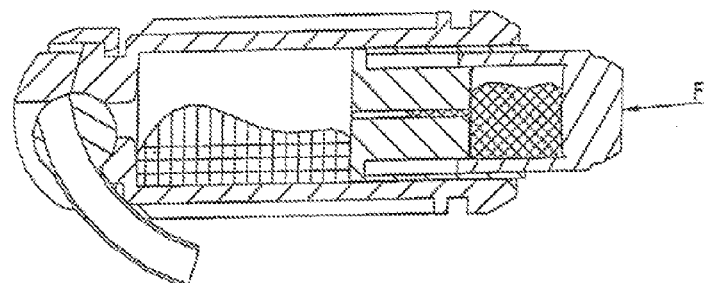

The operation of the mixing and application capsule of FIG. 9 according to the invention is shown in FIGS. 10a to 10d. The starting situation is shown in FIG. 10a, in which the capsule body 31 has a mixing chamber 32 with powder 41, the liquid container 21 has a liquid 42 and the passage plunger 11 is arranged between the mixing chamber 32 and liquid container 21. To activate the mixing and application capsule, the liquid container 21 is displaced in the direction of the passage plunger 11, so the blade 15 separates the foil 23 at its edge region and allows the liquid to flow away out of the cavity 22 into the through-channel 19 (FIG. 10b). In order to avoid the foil 23 sealing the hole of the through-channel 19 for the liquid 42, the liquid container 21 has channels at its inner surface, through which the liquid 42 can flow away, even if the foil 23 is placed on its surface. The channels of the liquid container 21 in this case correspond substantially to the elevations 16 of the surface of the projection 12 of the passage plunger 11.

Figure 10C:
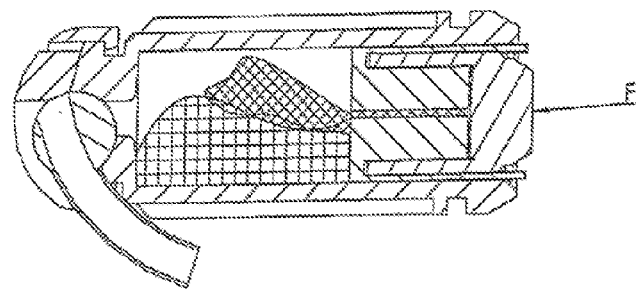
Figure 10D:
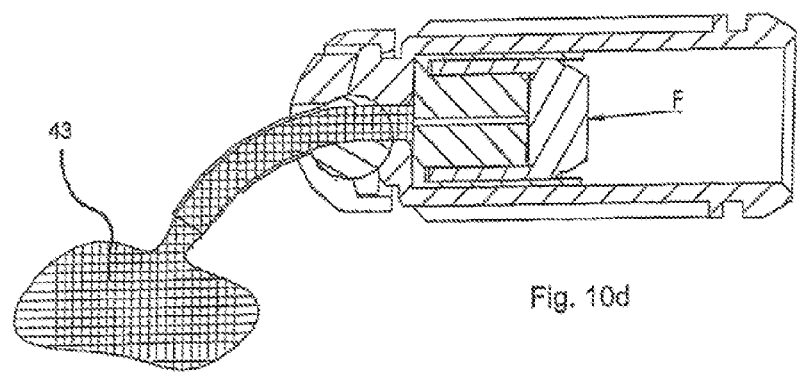

By further action of force on the liquid container 21 in the direction of the passage plunger 11, the cavity 22 is completely emptied of liquid and the liquid is pressed into the mixing chamber 32 to blend with the powder 41 (FIG. 10c). The dental preparation 43 is produced by mixing the powder 41 and the liquid 42 and through a further action of force on the liquid container 21 and the passage plunger 11 pushed out through the cannula 33 as a mixed paste 43 (FIG. 10d).

Figure 11A:
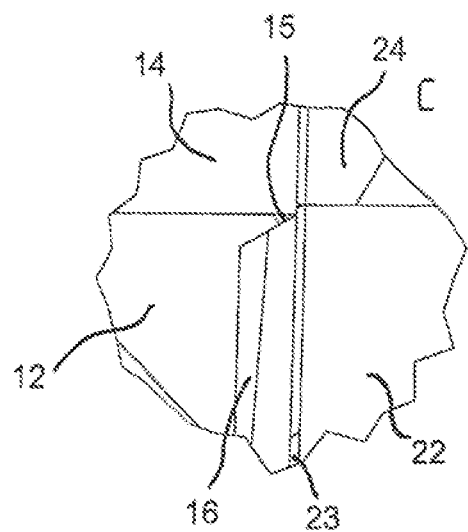
FIGS. 11a to 11e show detailed views of the mixing and application capsule of FIG. 9.

FIG. 11a shows a detailed view of the region C of FIG. 9. Shown in this detailed view is the projection 12 of the passage plunger 11, which has a radial peripheral blade 15. Proceeding from the hole of the through-channel 19 up to the blade 15, elevations 16 are arranged in the radial direction of the projection 12.

Figure 11B:
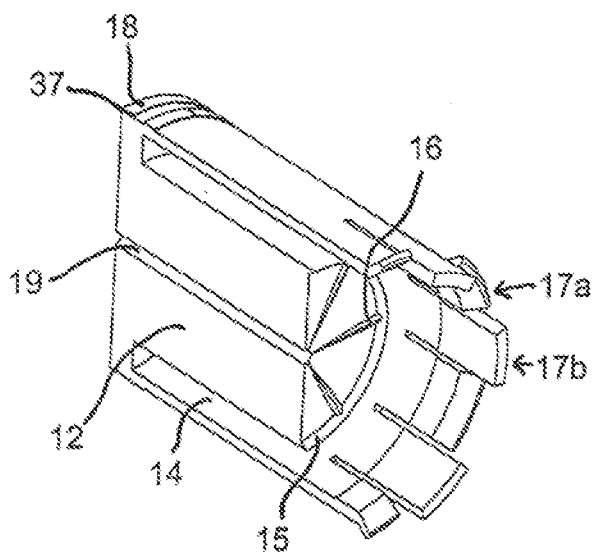
Figure 11C:
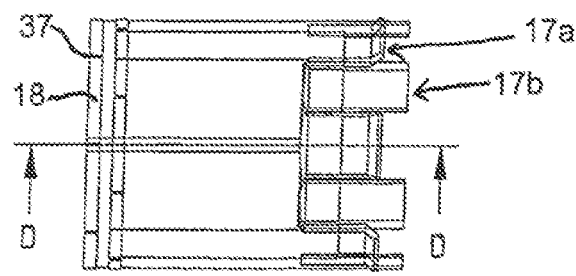
Figure 11D:
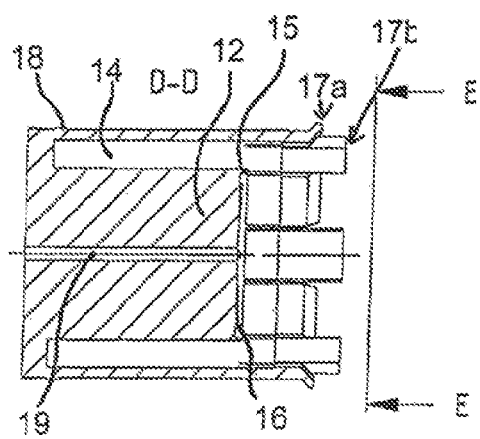
Figure 11E:
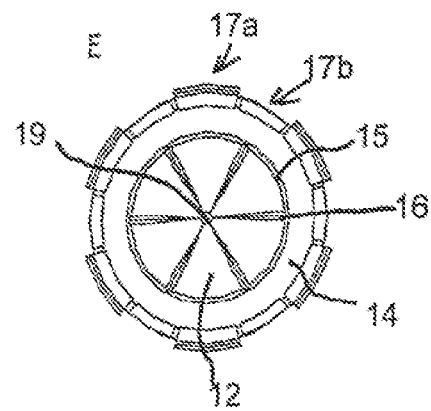

FIG. 11b shows a semi-cut open detailed view of the passage plunger 11 of the embodiment of FIG. 9. The passage plunger 11 has a cylindrical projection 12, in the interior of which is arranged the through-channel 19. Arranged on the surface of the projection 12 facing the liquid container 21 is an annular blade 15. The blade 15 is preferably funnel-shaped to assist a targeted discharge of the liquid 42. Arranged between the blade 15 and the through-channel 19 in the radial direction are elevations 16 for removing the liquid. Furthermore, the elevations 16, in combination with the corresponding channels on the inner surface of the liquid container 21 prevent the foil 23 from sealing the through-channel 19. FIGS. 11c to 11e show further detailed views of the passage plunger 11 of FIG. 9 according to the axes shown. Instead of the elevations drawn, indentations or channels are alternatively conceivable, which are used for the same purpose.

Furthermore, FIG. 11c shows a protrusion 18 with venting slots 37. This arrangement is implemented twice one behind the other in this example, the venting slots 37 not being aligned with one another and therefore forming a labyrinth seal.

Figure 12:
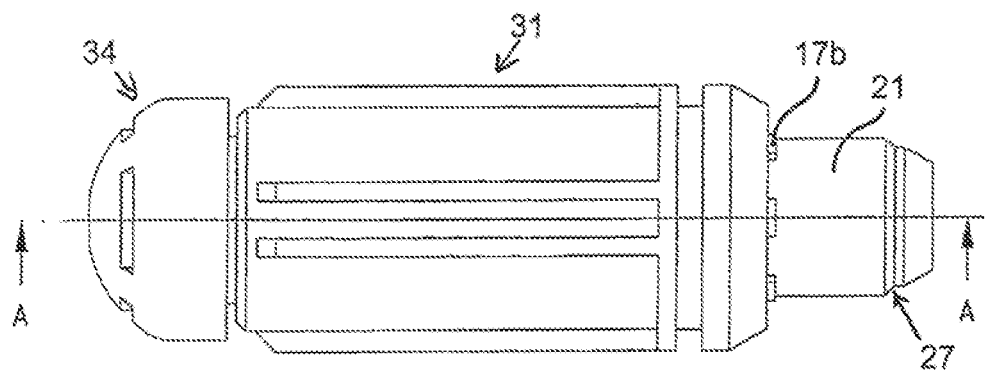
FIG. 12 shows an overall view of a mixing and application capsule according to the invention.

FIG. 12 shows an outer view of the mixing and application capsule according to the invention. The capsule body 31 is shown, on the first end of which the cap 34 is located. The second end of the capsule body 31 is configured open to receive the passage plunger 11 and the liquid container 21. The passage plunger 11, as described above, has tabs 17b which are oriented parallel to the longitudinal axis, i.e. straight, and bent tabs 17a, which only allow a displacement of the passage plunger 11 in the direction of the mixing chamber 32 if a predetermined force acts on the passage plunger 11 or the liquid container 21. The straight tabs 17b can be seen in FIG. 12, whereas the bent tabs 17a are not shown as they engage in the annular notch 36 of the capsule body. The bent tabs 17a mean that upon an action of force on the liquid container 21 along the longitudinal axis of the mixing and application capsule, the liquid container 21, in a first step, is pushed onto the passage plunger 11, without the passage plunger 11 being pushed into the mixing chamber 32, and in that, in a second step, in which the liquid 42 is already pressed out of the cavity 22 by introducing the projection 12, the passage plunger 11 moves into the mixing chamber 32. The straight tabs 17b are used for better guidance of the liquid plunger 21 and prevent it from undesired tilting.

Figure 13:
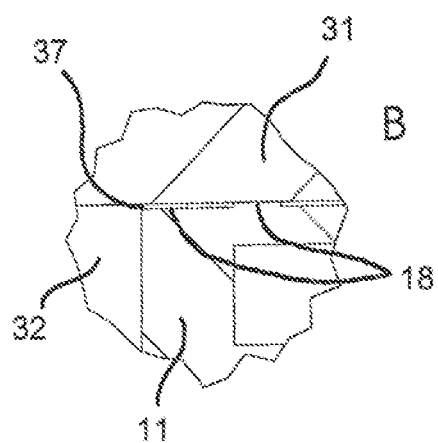
FIG. 13 shows a detailed view of the seal between the first plunger body and capsule body of a mixing and application capsule according to the invention.

FIG. 13 shows a detailed view of the region B of FIG. 9 between the capsule body 31 and the passage plunger 11. The passage plunger 11 has a protrusion 18, which is used for sealing between the mixing chamber 32 and the outer region of the mixing and application capsule. The protrusion 18 has venting slots 37, which allow a pressure compensation to be provided upon a telescoping of the telescopic cylinder between the mixing chamber 32 and outer region of the mixing and application capsule. The passage plunger 11 optionally has a plurality of radially arranged protrusions 18, which are in each case interrupted by venting slots 37, so a venting labyrinth is produced, which is easy for gas to penetrate, but not for the powder or fluid and the dental compound produced.

In addition or alternatively, the mixing and application capsule according to the invention has a gas-permeable membrane, for example in the cap region 34, through which a venting of the mixing chamber 32 takes place on insertion of the liquid plunger 21 into the passage plunger 11 and insertion of the passage plunger 11 into the mixing chamber 32. The gas-permeable membrane is, in this case, impermeable to the powdery component 41, the fluid 42 and the mixed dental preparation compound 43.

Venting devices such as the venting slot 37 and/or the venting membrane mean that the pressure built up by activating the mixing and application capsule in the mixing chamber 32 can rapidly be relieved, so it is made easier for the liquid 42 to flow into the mixing chamber 32. Furthermore, the exertion of force to insert the liquid container 21 and the passage plunger 11 is simultaneously reduced. By rapidly removing the air from the interior of the capsule body 31 both in the mixing chamber 32 and in the cavity between the passage plunger 11 and liquid container 21 it is achieved that the liquid 42 is not, in particular, distributed in the region between the passage plunger 11 and liquid container 21. This intermediate space remains dry, even if the foil 23 is not opened in its central region but in a radial region.

Figure 14A:
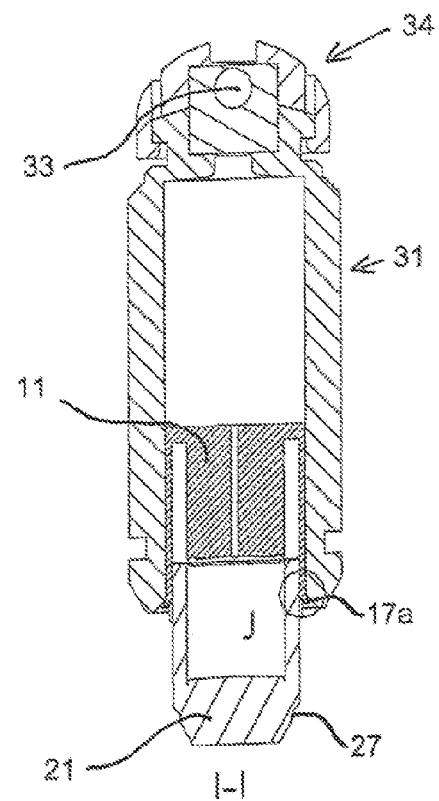
FIGS. 14a to 14c show a cross section and detailed views of a mixing and application capsule according to the invention before activation.

FIG. 14a shows a cross section of a mixing and application capsule according to the invention, with the aid of which the operation of the tabs 17a bent outward is explained. A mixing and application capsule according to the invention has, as is explained above, a capsule body 31, a passage plunger 11 and a liquid container 21. The cap and cannula arrangement 33, 34 is used to discharge the dental preparation 43 produced. The region between the capsule body 31, passage plunger 11 and liquid container 21 is shown in detail in FIG. 14b.

Figure 14B:
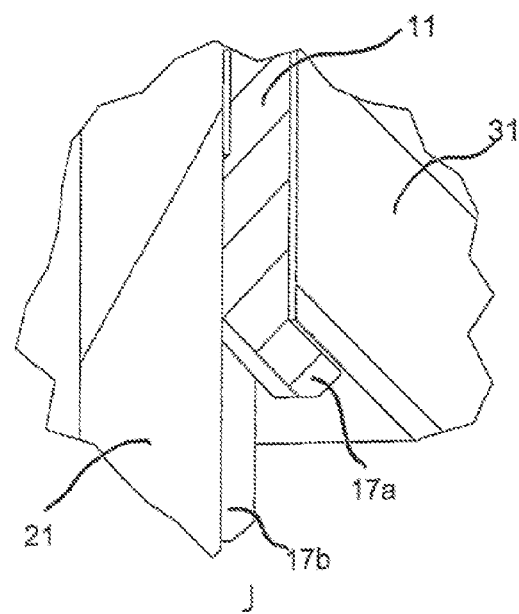
Figure 14C:
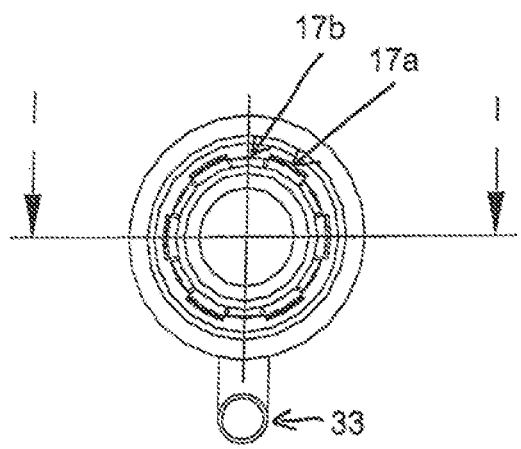
Figure 15A:
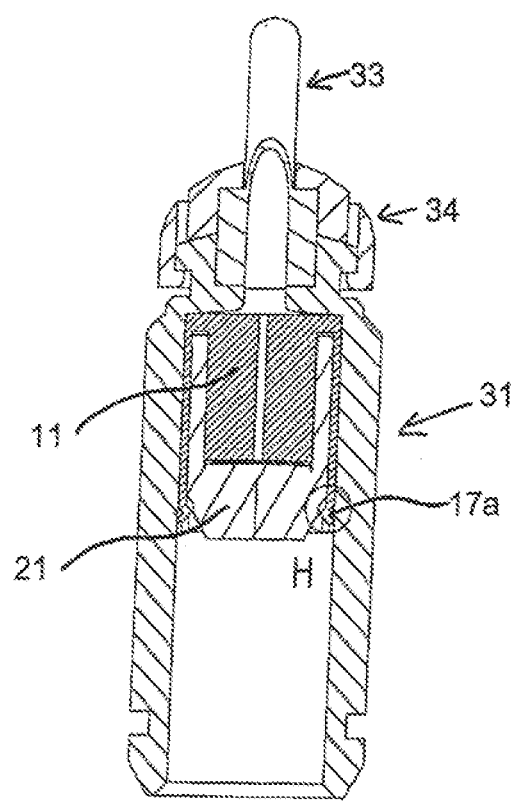
FIGS. 15a to 15c show the mixing and application capsule of FIGS. 14a to 14c after activation and discharge of the dental compound.
Figure 15B:
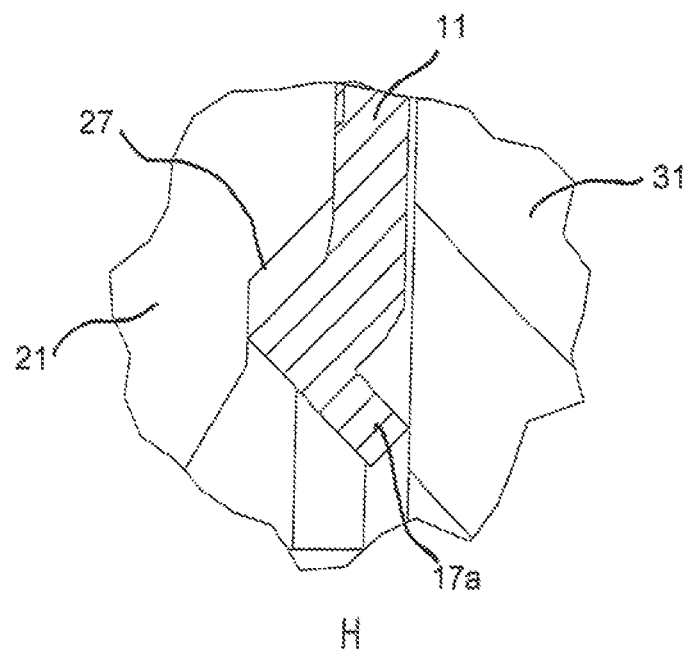
Figure 15C:
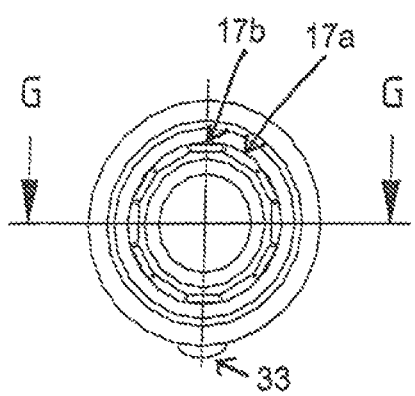

With the arrangement shown in FIG. 14b of the resistor elements 17a arranged projecting radially outwardly, the passage plunger 11 is prevented during the activation process of being displaced unintentionally into the mixing chamber 32 even if the liquid 42 in the cavity 22 has not yet been completely pressed out. A plurality of outwardly bent tabs 17a are arranged at the rear end of the passage plunger 11, i.e. at that end of the passage plunger 11 which is remote from the mixing chamber 32. The straight tabs 17b, which are oriented parallel to the longitudinal axis of passage plunger 11, are used, in particular, to guide the passage plunger 11 inside the capsule body 31.

If the liquid container 21 is displaced in the direction of the passage plunger 11, the outwardly bent tabs 17a hinder the passage plunger 11 from entering further into the capsule body 31. It is achieved, by means of the outwardly bent tabs 17a, that the external diameter of the passage plunger 11 is at least partially larger than the internal diameter of the plunger body 31. In the embodiment shown in FIGS. 14a to 14c and 15a to 15c, the bent tabs 17a project into the outer area of the mixing and application capsule. However, an annular groove may optionally be arranged in the interior of the capsule body 31, in which the bent tabs 17a engage in the same manner as is illustrated in FIG. 14b at the outer region of the plunger body 31.

The bent tabs 17a in the indentation 27 of the liquid container 21 only obtain space to release the movement of the passage plunger 11 into the mixing chamber 32 when the liquid container 21 has been inserted completely into the passage plunger 11. The indentation 27 is preferably configured as a reduced diameter at the rear end of the liquid container 21. In this case, the arrangement of the indentation 27 on the liquid container 21 corresponds to the state when the projection 12 has emptied the cavity 22. The straight tabs 17b are used both to guide the passage plunger 11 inside the capsule body 31 and also to guide the liquid container 21 inside the passage plunger 11.

According to the invention, further embodiments are provided, in which the through-channel 19 is arranged parallel to the longitudinal axis of the passage plunger 11. It is also possible to configure the through-channel 19 in another orientation inside the passage plunger 11 in order to transfer the liquid 42 from the cavity 22 into the mixing chamber 32 of the capsule body 31. Other geometric configurations of the projection 12 than those shown in the figures, and in a corresponding manner, of the cavity 22, are conceivable, such as, for example, pyramid-shaped, cylindrical, conical forms. The opening of the foil 23 preferably takes place by punching out, pushing open, cutting open or other opening mechanisms, which are based on the pressure effect on the liquid container 21 relative to the passage plunger 11. An opening of the foil 23 may take place in the centre or else in the edge regions. It is optional for the embodiments of FIGS. 1, 4 and 9 to have a liquid capsule 50 or for the liquid container 21 of FIG. 6 to be used without a separate liquid capsule 50.

The invention claimed is:

1. A mixing and application capsule for producing a dental preparation (43), wherein the mixing and application capsule comprises: a capsule body (31) with a mixing chamber (32) for receiving a mixing component (41) and for mixing the dental preparation (43) from the mixing component (41) and a fluid (42), and with an outlet opening (33) for discharging the dental preparation (43),
 a first plunger body (11) which can be displaced in the capsule body (31), delimits the mixing chamber (32) in the capsule body (31), said first plunger body (11) comprising a projection (12) having an interior channel (19) passing therethrough, and an edge recess (14), wherein a cavity (22) of a second plunger body (21) is in fluid communication with the mixing chamber (32) through the interior channel (19), and
 the second plunger body (21), comprises a central projection (25) and an edge projection (24), wherein the interior channel (19) is adapted to receive the central projection (25) and the edge recess (14) is adapted to receive the edge projection (24), wherein the edge recess (14) and the edge projection (24) are slidably coupled to form a seal of the cavity (22), wherein the cavity (22) of the second plunger body (21) is configured to receive the projection (12) of the first plunger body (11).

2. The mixing and application capsule as claimed in claim 1, wherein an end of the first plunger body (11) delimiting the mixing chamber (32), when the dental preparation (43) is discharged, acts as a plunger to push the mixed dental preparation (43) out of the capsule body (31).

3. The mixing and application capsule as claimed in claim 1, further comprising a liquid capsule, wherein the cavity (22) is configured to receive the liquid capsule.

4. The mixing and application capsule as claimed in claim 3, wherein the liquid capsule is sealed with a foil (23).

5. The mixing and application capsule as claimed in claim 4, wherein the foil (23) has at least one layer that at least partially comprises a metal layer.

6. The mixing and application capsule as claimed in claim 3, wherein the liquid capsule at least partially comprises a metal.

7. The mixing and application capsule as claimed in claim 3, wherein the projection (12) of the first plunger body (11) is equipped to open the liquid capsule.

8. The mixing and application capsule as claimed in claim 3, wherein the central projection (25) is adapted to open the liquid capsule.

9. The mixing and application capsule as claimed in claim 3, wherein the projection (12, 25) of the first and/or second plunger body (11, 21) is configured to puncture the liquid capsule.

10. The mixing and application capsule as claimed in claim 1, wherein the second plunger body (21) is configured as a liquid capsule.

11. The mixing and application capsule as claimed in claim 1, wherein the mixing and application capsule, in particular the first plunger body (11), has a resistor element (17a) for controlled prevention of a displacement of the first plunger body (11) into the capsule body (31).

12. The mixing and application capsule as claimed in claim 1, wherein the capsule body (31) comprises a venting device for removing a gas from the mixing chamber (32) of the capsule body (31).

13. The mixing and application capsule as claimed in claim 1, wherein the channel (19) comprises means for preventing the mixing component (41) from the mixing chamber (32) from entering the channel (19).

14. The mixing and application capsule as claimed in claim 13, wherein the means for preventing the mixing component (41) from the mixing chamber (32) from entering the channel (19) comprises a check valve, a flexible check flap, a porous structure, a gap and/or a tearable membrane.

15. The mixing and application capsule as claimed in claim 1, wherein the outlet opening (33) comprises a cannula, which, on its inside, has means for arranging an extension.

\* \* \* \* \*